(12) United States Patent
Hofer et al.

(10) Patent No.: US 7,582,081 B2
(45) Date of Patent: *Sep. 1, 2009

(54) SYSTEMS AND METHODS FOR CORNEAL SURFACE ABLATION TO CORRECT HYPEROPIA

(75) Inventors: Richard A. Hofer, Santa Cruz, CA (US); Stephen J. Koons, Palo Alto, CA (US); John Karl Shimmick, Belmont, CA (US)

(73) Assignee: AMO Manufacturing USA, LLC, Santa Clara, CA (US)

( * ) Notice: Subject to any disclaimer, the term of this patent is extended or adjusted under 35 U.S.C. 154(b) by 1675 days.

This patent is subject to a terminal disclaimer.

(21) Appl. No.: 09/950,563

(22) Filed: Sep. 10, 2001

(65) Prior Publication Data

US 2002/0045889 A1  Apr. 18, 2002

Related U.S. Application Data

(63) Continuation of application No. 09/379,372, filed on Aug. 23, 1999, now Pat. No. 6,319,247, which is a continuation-in-part of application No. 08/968,380, filed on Nov. 12, 1997, now Pat. No. 6,203,539, which is a continuation-in-part of application No. 08/906,020, filed on Aug. 5, 1997, now abandoned, which is a continuation of application No. 08/058,599, filed on May 7, 1993, now abandoned.

(51) Int. Cl.
*A61F 9/008* (2006.01)
(52) U.S. Cl. .............................. 606/5; 606/13
(58) Field of Classification Search ................ 606/3, 606/5, 10–12
See application file for complete search history.

(56) References Cited

U.S. PATENT DOCUMENTS 4,461,294 A  7/1984  Baron (Continued)

FOREIGN PATENT DOCUMENTS

DE  4232915  4/1994

(Continued)

OTHER PUBLICATIONS

Color Atlas of Excimer Laser Surgery F Thompson & P. McDonnell—E-ds pp. 53-54.*

(Continued)

*Primary Examiner*—David Shay

(57) ABSTRACT

Systems, methods and apparatus for performing selective ablation of a corneal surface of an eye to effect a desired corneal shape, particularly for correcting a hyperopic/astigmatic condition by laser sculpting the corneal surface to increase its curvature. In one aspect of the invention, a method includes the steps of directing a laser beam onto a corneal surface of an eye, and changing the corneal surface from an initial curvature having hyperopic and astigmatic optical properties to a subsequent curvature having correctively improved optical properties. Thus, the curvature of the anterior corneal surface is increased to correct hyperopia, while cylindrical volumetric sculpting of the corneal tissue is performed to correct the astigmatism. The hyperopic and astigmatic corrections are preferably performed by establishing an optical correction zone on the anterior corneal surface of the eye, and directing a laser beam through a variable aperture element designed to produce a rectangular ablation (i.e., cylindrical correction) on a portion of the optical correction zone. The laser beam is then displaced by selected amounts across the optical correction zone to produce a series of rectangular ablations on the correction zone that increases the curvature of the corneal surface to correct the hyperopic refractive error.

5 Claims, 5 Drawing Sheets

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,718,418 A * | 1/1988 | L'Esperance, Jr. | 606/5 |
| 4,729,372 A | 3/1988 | L'Esperance, Jr. | |
| 4,732,148 A * | 3/1988 | L'Esperance, Jr. | 606/5 |
| 4,770,172 A | 9/1988 | L'Esperance, Jr. | |
| 4,773,414 A | 9/1988 | L'Esperance, Jr. | |
| 4,798,204 A | 1/1989 | L'Esperance, Jr. | |
| 4,838,266 A | 6/1989 | Koziol et al. | |
| 4,840,175 A | 6/1989 | Peyman | |
| 4,901,718 A | 2/1990 | Bille et al. | |
| 4,903,695 A | 2/1990 | Warner et al. | |
| 4,907,586 A | 3/1990 | Bille et al. | |
| 4,911,711 A | 3/1990 | Telfair et al. | |
| 4,973,330 A | 11/1990 | Azema et al. | |
| 5,074,859 A | 12/1991 | Koziol | |
| 5,090,798 A | 2/1992 | Kohayakawa | |
| 5,108,388 A | 4/1992 | Trokel | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,219,344 A | 6/1993 | Yoder, Jr. | |
| 5,284,477 A | 2/1994 | Hanna et al. | |
| 5,342,351 A | 8/1994 | Blaha et al. | |
| 5,411,501 A | 5/1995 | Klopotek | |
| 5,461,212 A | 10/1995 | Seiler et al. | |
| 5,556,395 A | 9/1996 | Shimmick et al. | |
| 5,624,436 A | 4/1997 | Nakamura et al. | |
| 5,637,109 A | 6/1997 | Sumiya | |
| 5,642,287 A | 6/1997 | Sotiropoulos et al. | |
| 5,646,791 A | 7/1997 | Glockler | |
| 5,683,379 A | 11/1997 | Hohla | |
| 5,713,892 A | 2/1998 | Shimmick | |
| 5,814,042 A | 9/1998 | Zair | |
| 5,827,264 A | 10/1998 | Hohla | |
| 6,319,247 B1 * | 11/2001 | Hofer et al. | 606/3 |

FOREIGN PATENT DOCUMENTS

| | | |
|---|---|---|
| EP | 0529822 | 3/1993 |
| EP | 0628298 A1 | 12/1994 |
| EP | 0296982 | 12/1998 |
| FR | 2633826 | 1/1990 |
| GB | 2221162 | 1/1990 |
| WO | WO 91/08723 | 6/1991 |
| WO | WO 91/11158 | 8/1991 |
| WO | WO 92/13507 | 8/1992 |
| WO | WO 93/08877 | 5/1993 |
| WO | WO 93/14430 | 7/1993 |

OTHER PUBLICATIONS

Munnerlyn et al., Photoreactive Keratectomy: A technique for laser refractive surgery; J. Cataract Refract. Surf., 1998 14:46-52.

Sher et al., Clinical Use of the 193-nm Excimer Laser in the Treatment of Corneal Scars, Arch. Ophthalmology, Apr. 1991, vol. 109, pp. 491-498.

Stark et al., Clinical Follow-up of 193-nm ArF Excimer Laser Photokeratectomy, Ophthalmology, May 1992, vol. 99, No. 5, pp. 805-812.

* cited by examiner

SYSTEMS AND METHODS FOR CORNEAL SURFACE ABLATION TO CORRECT HYPEROPIA

CROSS-REFERENCES TO RELATED APPLICATIONS

The present application is a continuation application of U.S. patent application Ser. No. 09/379,372 filed Aug. 23, 1999 now U.S. Pat. No. 6,319,247, which is a continuation-in-part of U.S. patent application Ser. No. 08/906,020 filed on Aug. 5, 1997 now abandoned, which is a continuation-in-part of U.S. patent application Ser. No. 08/968,380 filed on Nov. 12, 1997 now U.S. Pat. No. 6,203,539, which is a continuation of U.S. patent application Ser. No. 08/058,599 filed on May 7, 1993 now abandoned, the full disclosures of which are incorporated herein by reference.

BACKGROUND OF THE INVENTION

The present invention is directed to systems, methods and apparatus for performing selective ablation of a corneal surface of an eye to effect a desired corneal shape. In particular, the present invention is directed to methods for correcting a hyperopic condition of the eye by laser sculpting the corneal surface to increase its curvature.

Ultraviolet and infrared laser based systems and methods are known for enabling ophthalmological surgery on the external surface of the cornea in order to correct vision defects. These procedures generally employ an ultraviolet or infrared laser to remove a microscopic layer of an anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without heating the remaining substrate; the mechanism of the ablation is photochemical, i.e. the direct breaking of intermolecular bonds. The ablation removes a layer of the stroma to change its contour for various purposes, such as correcting myopia, hyperopia, and astigmatism. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. Patent application Ser. No. 109,812 filed Oct. 16, 1987 for "LASER SURGERY METHOD AND APPARATUS"; U.S. Pat. No. 5,163,934 issued Nov. 17, 1992 for "PHOTOREFRACTIVE KERATECTOMY"; U.S. patent application Ser. No. 08/368,799, filed Jan. 4, 1995 for "METHOD AND APPARATUS FOR TEMPORAL AND SPATIAL BEAM INTEGRATION"; U.S. patent application Ser. No. 08/138,552, filed Oct. 15, 1993 for "METHOD AND APPARATUS FOR COMBINED CYLINDRICAL AND SPHERICAL EYE CORRECTIONS"; and U.S. patent application Ser. No. 08/058,599, filed May 7, 1993 for "METHOD AND SYSTEM FOR LASER TREATMENT OF REFRACTIVE ERRORS USING OFFSET IMAGING".

The technique for increasing the curvature of the corneal surface for hyperopia error correction involves selectively varying the area of the cornea exposed to the laser beam radiation to produce an essentially spherical surface profile of increased curvature. This selective variation of the irradiated area may be accomplished in a variety of ways. For example, U.S. Pat. No. 4,665,913 cited above discloses the technique of scanning the region of the corneal surface to be ablated with a laser beam having a relatively small cross-sectional area (compared to the optical zone to be ablated) in such a manner that the depth of corneal removal increases with distance from the intended center of ablation. This is achieved by scanning the beam more times over the deeper regions than the shallower regions. As pointed out in U.S. Pat. No. 5,163,934, such ablations tend to be rougher than area ablations. The result is a new substantially spherical profile for the anterior corneal surface with maximum depth of cut at the extreme outer boundary of the optical zone. Another technique disclosed in the above-cited U.S. Pat. No. 4,732,148 employs a rotatable mask having a plurality of elliptical annular apertures which are progressively inserted into the laser beam path to provide progressive shaping of the laser beam in order to achieve the desired profile.

One of the major difficulties encountered in the application of laser surgery techniques to effect hyperopic refractive error corrections lies in the nature of the boundary between the optical zone and the untreated area. Since the anterior surface of the cornea is sculpted during the process to have an increased curvature, the maximum depth of cut necessarily occurs at the outer boundary of the optical zone. The generally annular region between this outer boundary and the adjacent untreated anterior surface portion of the cornea typically exhibits steep walls after the completion of the photoablation procedure. After the surgery, the tendency of the eye is to eliminate these steep walls by stimulated healing response involving concurrent epithelial cell growth and stromal remodeling by the deposition of collagen, which results in corneal smoothing by filling in tissue in the steep walled region. This natural healing response acts to eliminate the discontinuity, resulting in a buildup of tissue in the steep walled region and over the outer portion of the optical zone. This natural phenomenon, sometimes termed the "hyperopic shift" in phototherapeutic keratectomy, causes a lack of precision for a given surgical procedure and diminished predictability, which tend to counteract the beneficial effects of the refractive correction procedure and thereby reduce the desirability of the procedure to the prospective patient.

In some patients, there are both hyperopia and astigmatism defects in the same eye, requiring correction of both errors in order to improve vision. Astigmatic conditions are typically caused by a cylindrical component of curvature departing from the otherwise generally spherical curvature of the surface of the cornea. Astigmatic conditions are usually corrected by effecting cylindrical ablation about the axis of cylindrical curvature of the eye. These cylindrical ablations tend to increase the sharp transitions in the cornea at the extreme ends of the sculpted area.

What is needed in the field of ophthalmological surgery, therefore, are systems and methods for correcting both hyperopia and astigmatism of the eye by laser removal of the corneal surface. It would be particularly desirable to perform such hyperopia and astigmatism corrections without generating steep walls in the region between the outer boundary of the optical zone and the adjacent untreated anterior surface portion of the cornea.

SUMMARY OF THE INVENTION

The present invention is directed to systems, methods and apparatus for performing selective ablation of a corneal surface of an eye to effect a desired corneal shape, such as for correcting a hyperopic condition by laser sculpting the corneal surface to increase its curvature. The present invention is particularly useful for correcting hyperopic conditions with a cylindrical component of curvature (i.e., astigmatism). However, it will be appreciated that the systems and methods of the present invention can be applied equally well to the correction of other refractive procedures, such as myopia, irregular astigmatism, or combinations thereof.

In one aspect of the invention, a method includes the steps of directing a laser beam onto a corneal surface of an eye, and changing the corneal surface from an initial curvature having hyperopic and astigmatic optical properties to a subsequent curvature having correctively improved optical properties. Thus, the curvature of the anterior corneal surface is increased to correct hyperopia, while cylindrical volumetric sculpting of the corneal tissue is performed to correct the astigmatism. The hyperopic and astigmatic corrections are preferably performed by establishing an optical correction zone on the anterior corneal surface of the eye in which the desired refractive correction is to be effected, and an annular transition zone around the optical correction zone. A laser beam is directed through a variable aperture element that is designed to generate a profiled beam with a generally rectangular shape on the cornea (i.e., cylindrical correction). The profiled beam is directed onto the corneal surface and displaced by selected amounts across the optical correction zone to produce a series of rectangular ablations on the correction zone. The locations of the rectangular ablations on the optical correction zone are selected to increase the curvature of the corneal surface to correct the hyperopic refractive error. The angle of the rectangular ablations are determined by the axis of the desired cylindrical correction.

The technique for increasing the curvature of the corneal surface for hyperopia error correction involves selectively varying the area of the cornea exposed to the laser beam radiation to produce a surface profile of increased curvature. Thus, the rectangular ablations generated by the profiled beam are displaced across the cornea such that the depth of corneal removal increases with distance from the intended center of ablation, or the central axis of the optical correction zone. In one embodiment, the rectangular ablations are sized and displaced such that the outer edge of the optical correction zone (which is the portion that should receive the deepest corneal removal) will be subjected to a substantial portion (if not all) of the rectangular ablations. In addition, the central portion of the optical correction zone (which is desirably the portion that receives the least amount of corneal removal) receives the least amount of the ablations. The intermediate areas of the optical correction zone will receive an appropriate amount of rectangular ablations such that the corneal surface curvature increases in the radially outward direction to correct for hyperopia.

In a preferred implementation of the method, the laser beam passes through a variable width slit and a variable diameter diaphragm to create a profiled beam that is imaged onto the corneal surface. The slit width is varied in conjunction with the beam displacement to provide a surface profile of increased curvature within the optical correction zone, as discussed above. The diaphragm is maintained at a large enough diameter to minimize its effect on the optical correction zone. In addition, the variable diaphragm is varied in selected amounts to smooth the sharp transitions at the ends of the cylindrical corrections. In an exemplary embodiment, the diaphragm decreases in diameter as the laser beam is displaced radially outward from a central axis of the correction zone, and increases in diameter as the laser beam is displaced radially inward toward the central axis. This provides a more gradual sloping of the corneal surface to eliminate the sharp discontinuity between the outer edge of the optical zone and the edge of the untreated area.

The rectangular ablations or cylindrical corrections may be created and displaced across the correction zone in a variety of different manners. In one embodiment, the laser beam passes through the variable aperture element to form a profiled beam that is imaged onto the cornea with an imaging lens positioned between the laser and the eye. The image of the profiled beam is displaced across the optical correction zone by first locating the lens at a starting position, pulsing the laser and then displacing the lens to a subsequent position, which is preferably the starting position plus a predetermined incremental amount. In other embodiments, the profiled beam may be scanned across the cornea with rotating mirrors (e.g., galvanometers), rotating prisms, or the like. Alternatively, the profiled beam may be displaced by moving the position of the variable aperture element. In this embodiment, the beam will be sized to cover the entire optical correction zone, and the variable aperture element will be sized to displace the beam across this zone.

For a fuller understanding of the nature and advantages of the invention, reference should be had to the ensuing detailed description taken in conjunction with the accompanying drawings.

DESCRIPTION OF THE SPECIFIC EMBODIMENTS

The present invention is directed to systems, methods and apparatus for performing selective ablation of a corneal surface of a patient's eye to effect a desired corneal shape. In a specific implementation, methods are provided for correcting a hyperopic condition by laser sculpting the corneal surface to increase its curvature. The present invention is particularly useful for correcting hyperopic conditions with a cylindrical component of curvature (i.e., astigmatism), while also smoothing the transition zone between the optical correction zone and the remainder of the cornea. For convenience, the remaining disclosure will be directed specifically to systems and methods for the correction of hyperopic and astigmatic refractive errors. However, it will be appreciated that the systems and methods of the present invention can be applied equally well to the correction of other refractive procedures, such as myopia, irregular astigmatism or combinations thereof.

Figure 1:
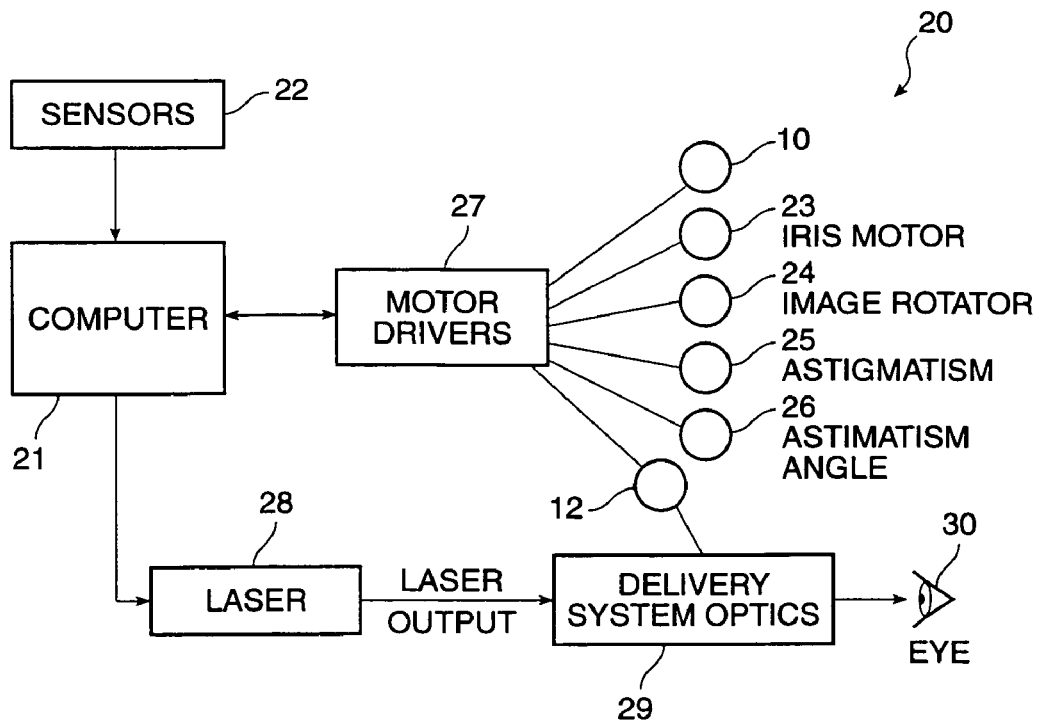
FIG. 1 is a block diagram of an ophthalmological surgery system for incorporating the invention.

FIG. 1 illustrates a block diagram of a representative ophthalmological surgery system for incorporating the invention. As shown, a laser surgery system 20 includes a computer 21, such as a personal computer work station or other conventional arrangements. The subcomponents of laser surgery system 20 are known components and preferably comprise the elements of the VISX STAR Excimer Laser System™, which is commercially available from VISX, Incorporated of Santa Clara, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, an astigmatism motor 25, an astigmatism angle motor 26, an image lens motor 12 and an image lens rotation motor 10. The feedback signals from sensors 22 are provided via appropriate signal conductors to the computer 21. The computer controls the operation of the motor drivers generally designated with reference numeral 27 for operating the elements 10, 12 and 23-26. In addition, computer 21 controls the operation of the Excimer laser 28, which is preferably an argon-fluorine laser with a 193 nanometer wavelength output designed to provide feedback stabilized fluence of 160 mJoules per cm2 at the cornea of the patient's eye 30 via the delivery system optics generally designated with reference numeral 29 and shown in FIG. 4. Other ancillary components of the laser surgery system 20 which are not necessary to an understanding of the invention, such as a high resolution microscope, a video monitor for the microscope, a patient eye retention system, and an ablation effluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 21. Further details of suitable system for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are hereby incorporated herein by reference.

Figure 2:
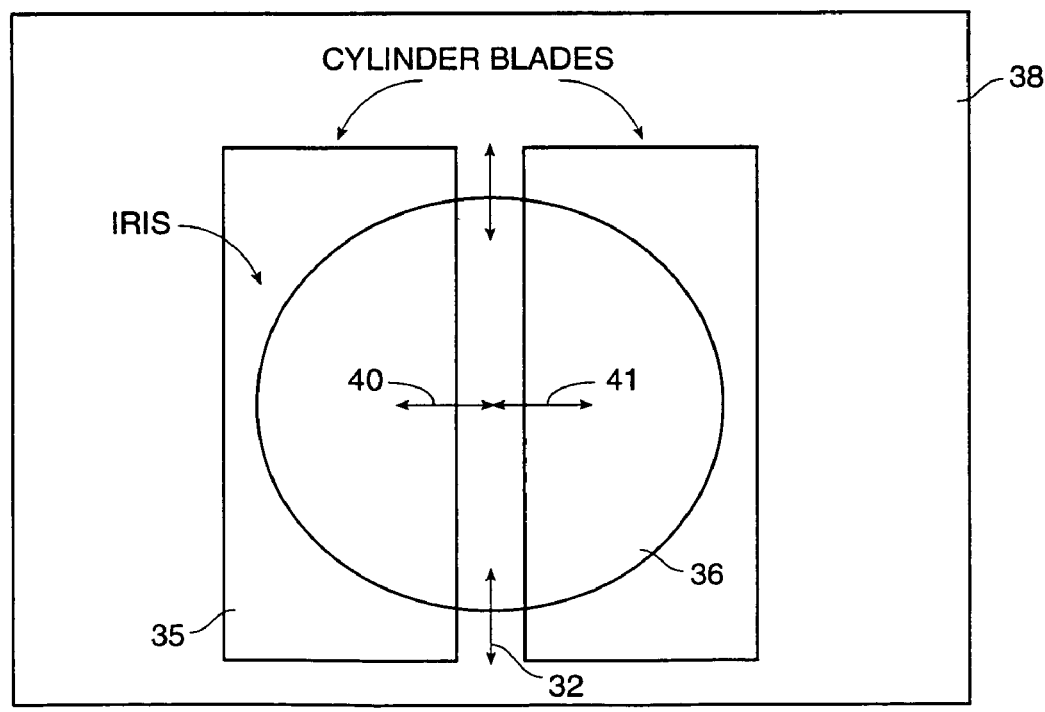
FIG. 2 is a schematic plan view illustrating a movable slit and variable diameter aperture used in the system of FIG. 1.

The iris motor 23 is used to control the diameter of a variable diameter iris schematically depicted in FIG. 2. The astigmatism motor 25 is used to control the separation distance between a pair of cylinder blades 35, 36 which are mounted on a platform 38 for bi-directional translational motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 2) with the appropriate coordinate axes of the patient's eye. Iris 32 is driven by iris motor 23 in a known way to change the diameter of the iris opening from a fully opened position (the position illustrated in FIG. 2) to a fully closed position in which the aperture is closed to a minimum diameter of 0.8 mm. It is understood that the variable diameter iris 32 and the cylinder blades 35, 36 are positioned with respect to the output of laser 28 in such a manner so that a profiled beam shape is imaged onto the corneal surface of the patient's eye 30. For the purpose of this application, it may be assumed that iris 32 and cylinder blades 35, 36 are part of the delivery system optics subunit 29 shown in FIG. 1.

Of course, it should be understood that the laser beam may be profiled in a variety of conventional or non-conventional manners other than that described above. For example, rotating masks, ablatable membranes and/or prisms may be used to image the laser beam rather than the variable apertures described above.

Figure 5:
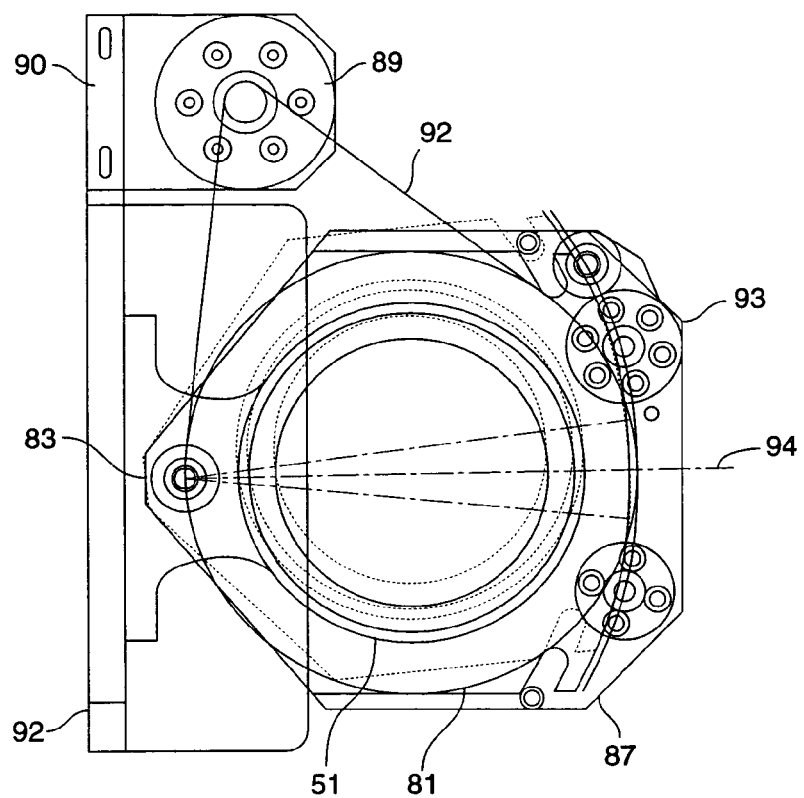
FIG. 5 is a top plan view of an image offset control unit of the invention, with the top annular portion removed.
Figure 6:
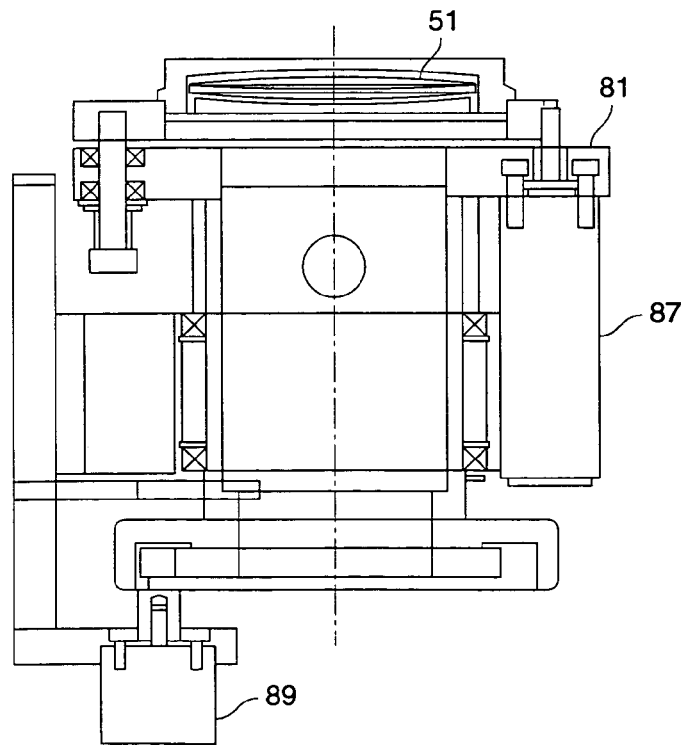
FIG. 6 is a side sectional view taken along lines 5-5 of FIG. 5.

The system of FIGS. 1 and 2 may be used according to the invention to effect hyperopic refractive error corrections to the anterior surface of the cornea. In addition, the methods of the present invention provide a smooth transition zone between the outer edge of the optical zone and the untreated surface of the cornea. With reference to FIGS. 5 and 6, an imaging lens 51 may be laterally offset or displaced from a central axis by a variable amount in the manner set forth more fully below. Lens 51 preferably comprises the existing imaging lens found in the delivery system optics 29 of the FIG. 1 system which are described more fully below. The image lens motor 12 is used to translate the lens 51 relative to the central axis and the image lens rotation 10 is used to rotate the lens 51 about the central axis. Displacing lens 51 by translating the lens in a radial direction off the central axis, which may or may not correspond to the laser beam axis, displaces the image of the aperture in a related manner. As discussed in more detail below, lens 51 may be displaced such that the image of the aperture is displaced across the optical correction zone to effect a series of rectangular ablations (i.e., cylindrical corrections) across the optical correction zone.

Of course, it will be recognized that the laser beam may be displaced or scanned across the optical correction zone with scanning elements other than the displaceable imaging lens described above. For example, the profiled beam may be scanned across the cornea with rotating mirrors (e.g., galvanometers), rotating prisms, or the like. Alternatively, the profiled beam may be displaced by changing the size of the iris 32 and cylinder blades 35, 36. In this embodiment, the beam will preferably be sized to cover the entire optical correction zone, and the cylinder blades 35, 36 will be independently movable so that the position of the image can be displaced across the cornea (e.g., by moving a single cylinder blade, or by moving both blades).

Figure 3A:
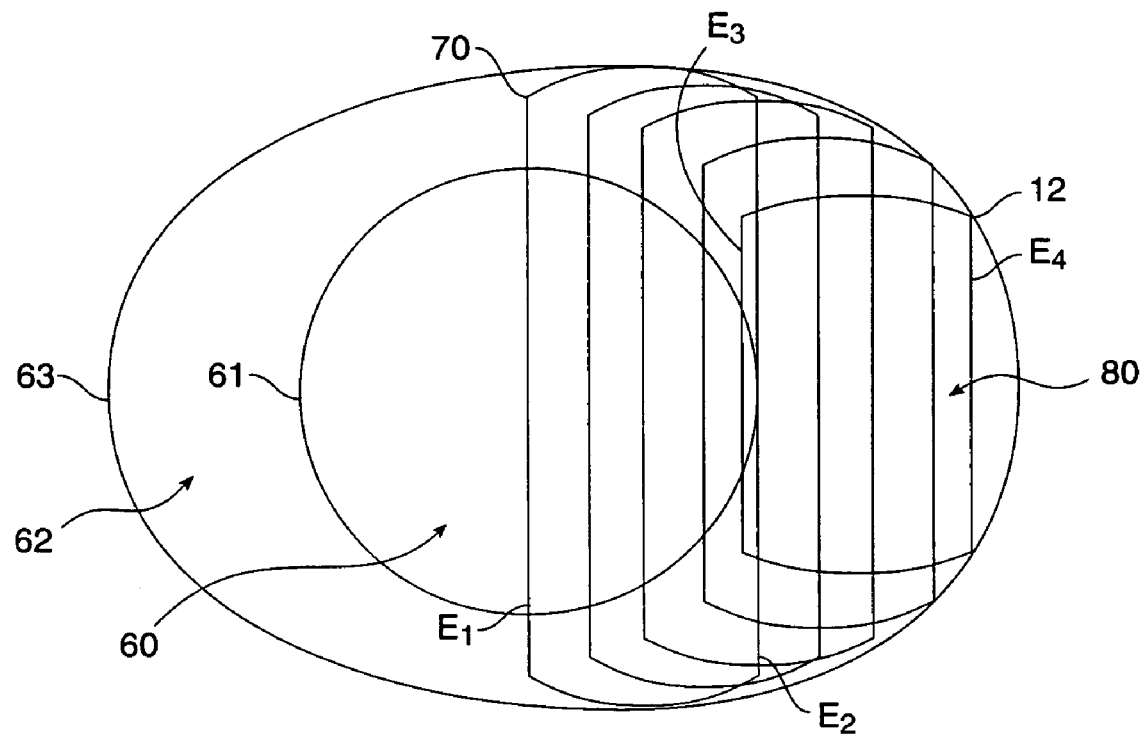
FIGS. 3A-3C are schematic views showing the ablation geometry for the aperture of FIG. 2.
Figure 3B:
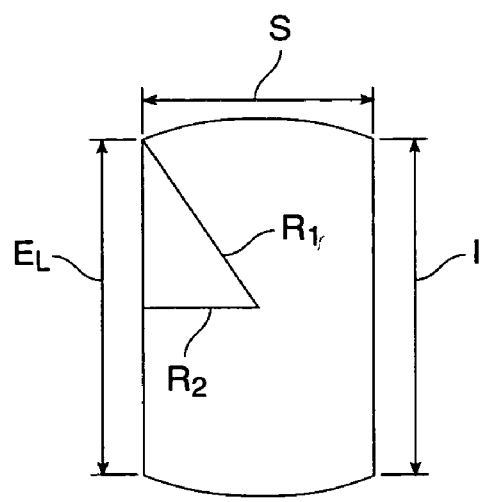

FIGS. 3A and 3B illustrate the method of the present invention for correcting hyperopic and astigmatic refractive errors. As shown, an optical correction zone 60 and an annular transition zone 62 are established on the corneal surface of the patient's eye. In these figures, the intended optical zone is the central region bounded by circle 61 and the intended transition zone is the annular region bounded by circles 61 and 63. Depending on the nature of the desired optical correction, optical correction zone 60 may or may not be centered on the center of the pupil or on the apex of the anterior corneal surface. The correction zone will typically have a radius $R_3$ of about 2 to 3 mm and transition zone 62 will have an outside radius of about 3 to 5 mm. As shown, transition zone 62 may have an elliptical shape, or it may be generally circular, depending on the desired optical correction.

Figure 3C:
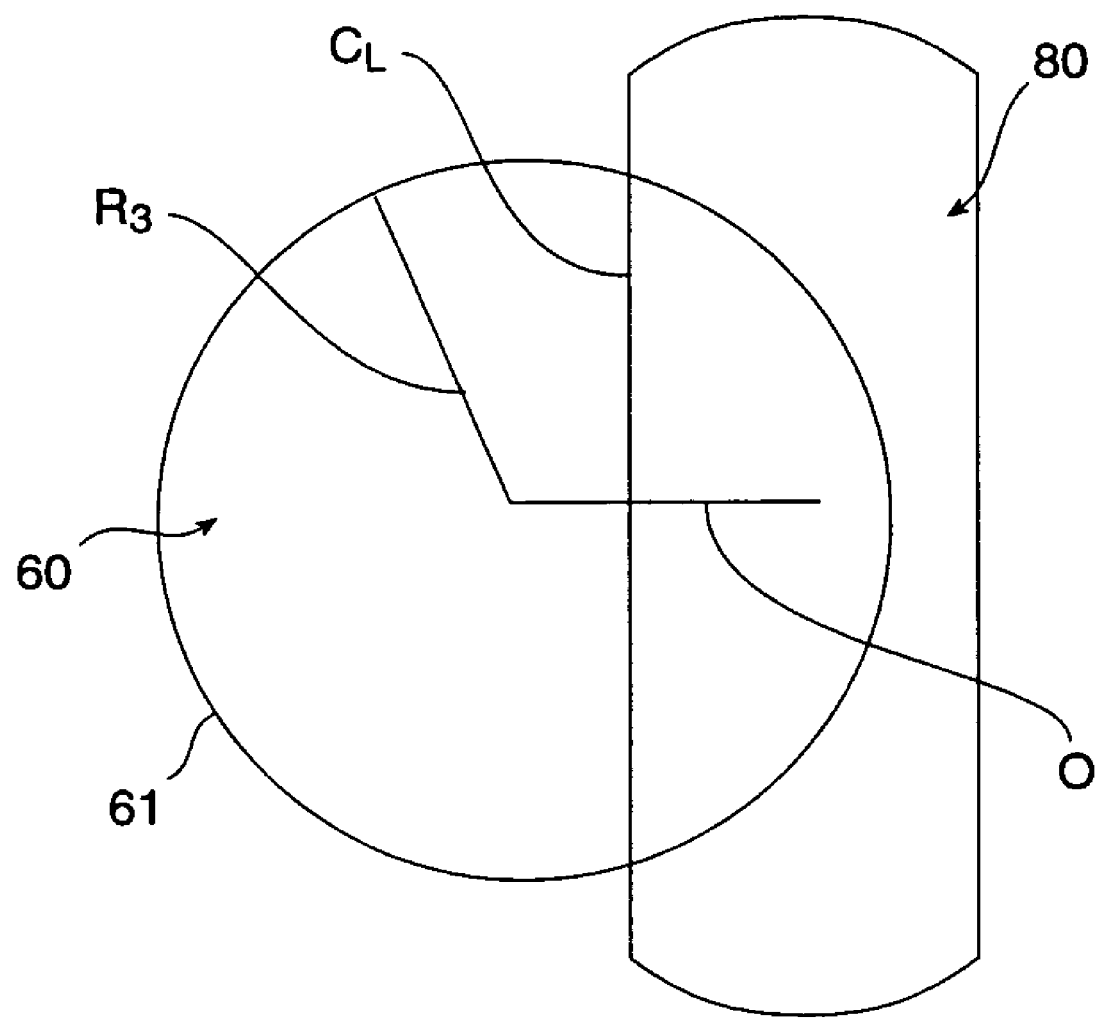

Referring to FIG. 3B, $R_2$ represents the half width of the slit between blades 35, 36, S represents the width of the slit between blades 35, 36, $R_1$ represents the radius of the iris 32, I is the diameter of the iris 32 and $E_L$ is the edge length of the blades 35, 36 which is established by the diameter of the iris 32. As shown in FIG. 3C, $R_3$ is the radius of the optical correction zone, $C_L$ is the half length of the optical correction zone and O represents the radial offset of the center of the image of the slit aperture relative to the center of optical correction zone 60. The radial offset O will increase as the imaging lens 51 is displaced away from the central axis and the half length of the optical correction zone $C_L$ will decrease as the rectangular ablations 80 move radially outward.

In the preferred embodiment, the laser beam will be profiled such that it provides a cylindrical correction with little to no spherical component within the optical correction zone. Thus, the curvature of the anterior corneal surface is increased to correct hyperopia, while cylindrical volumetric sculpting of the corneal tissue is performed to correct the astigmatism. The hyperopia cylinder surface is preferably created by using the offset mechanism to place a series of slit-shaped or generally rectangular ablations 80 over the optical correction zone of the eye, as shown in FIG. 3A. Thus, the rectangular ablations 80 are displaced across the cornea such that the depth of corneal removal increases with distance from the intended center of ablation, or the central axis of the optical correction zone 60. According to the present invention, the rectangular ablations 80 are sized and displaced such that the outer boundary 61 of the optical correction zone 60 (which is the portion that should receive the deepest corneal removal) will be subjected to a substantial portion (if not all) of the rectangular ablations 80. On the other hand, the rectangular ablations 80 are sized and displaced such that the central portion of the optical correction zone 60 (which is desirably the portion that receives the least amount of corneal removal) receives a small portion (e.g., one or zero) of the ablations.

The profiled beam may start at one side of the correction zone 60, and be displaced across the correction zone 60 to the other side. Alternatively, the profiled beam may start towards the center of the correction zone 60 (actually slightly offset from center as shown in FIG. 3A) and be displaced radially outward to place a series of cylindrical ablations 80 over one half of the eye. In this embodiment, the profiled beam will then be placed in the center of the correction zone (actually displaced in the opposite direction from center), and displaced radially outward in the opposite direction to cover the other half of the eye.

The slit width between cylinder blades 35, 36 and the iris diameter are preferably varied as the laser beam is displaced across the optical correction zone to smooth the surface of the transition zone. For hyperopic astigmatic corrections, the iris is maintained at a large enough diameter to minimize the effect of the aperture on the optical correction zone. For hyperopia with some spherical components, the spherical correction will preferably occur before or after the cylindrical corrections.

For a hyperopic dioptric correction of a given fixed value, the sequencing of the aperture is done in such a manner as to satisfy the hyperopic lens equations described in "Photorefractive Keratectomy: A technique for laser refractive surgery" authored by Munnerlyn et al., *J. Cataract Refract. Surg.* Vol. 14, pages 46-52 (January, 1988), the disclosure of which is hereby incorporated by reference. A fixed value of the dioptric correction is used to generate the cut profile c(r). The cut profile is given by the equation:

$$c(r) = -100 * (R_1 - R_2 - \sqrt{R_1^2 - y^2} + \sqrt{R_2^2 - y^2})$$

where $R_1$ is the initial radius of curvature, $R_2$ is the final radius of curvature and y is the distance from the center of the optical correction zone 60. The sequence of aperture dimensions is created by control of the diameter of iris 32 and the width of cylinder blades 35, 36 throughout the surgical procedure. The sequence of aperture dimensions may also be tailored to accommodate variations in the profile of the laser beam.

After the initial slit shape has been ablated on the corneal surface, the image of the aperture is displaced or scanned over the anterior surface of the cornea to selectively ablate the entire correction zone. While several different scanning sequences are possible, the following sequence has been actually implemented with effective results. The position of the inner edge $E_1$ of the slit shape for a particular pulse is determined by the hyperopia depth calculations of Munnerlyn as discussed above. A binary search of the radius is performed to determine the radius from the center of the correction zone where the depth of that radius is equal to the depth for the pulse number of the treatment. The inner edge position of the cylinder blades 35, 36 is generally equal to the offset O minus the slit radius $R_2$ and the outer edge position of the blades is equal to the offset O plus the slit radius $R_2$.

In the example shown in FIGS. 3A and 3B, the initial values of radial offset O, iris diameter I and slit width S are preferably selected so that the inner edge $E_1$ of blade 35 is initially coincident with the central axis of the optical correction zone 60, and the outer edge $E_2$ of blade 35 is initially located such that a portion of outer edge $E_2$ is substantially coincident with the outer boundary 61 of optical correction zone 60. The inner edge $E_1$ of blade 35 is positioned to create the exact curve on the eye to create the desired cylindrical correction. The iris diameter I is selected such that the ends 70 of the inner edge $E_1$ fall outside of the correction zone boundary 61, and the ends of outer edge $E_2$ fall inside of the outer boundary 62 of the transition zone 62. The iris diameter I should always be large enough such that the edge length $E_L$ of the slit shape is greater than the corrected length ($C_L \times 2$) to generate the correct cylindrical refraction in the optical correction zone.

Once the inside edge of each slit shape is found, the slit width S is calculated. The slit width S determines the position of the outside edge of the slit shape. Generally, the slit width S is dependent on the inside edge $E_1$ and the diameters of the correction and transition zones 60, 62. The initial slit width S will be calculated such that the initial outside edge $E_2$ is slightly outside of the outer boundary 61 of the optical correction zone. Thus, the outside edge start position is equal to the correction radius plus a correction margin $C_m$ or:

$$E_2 = R_3 + C_m$$

The correction margin smoothes the transition between the correction zone and the transition zone. The outside edge end position $E_4$ is preferably located at some margin $A_m$ inside the outer boundary 62 of the transition zone. Thus, $$E_4 = \text{Outer boundary diameter} + A_m$$

The outside edge position ($O_{EP}$) at any point during the procedure is generally found by:

$$O_{EP} = (((\text{OutsideEdgeEndPos}) - \text{OutsideEdgeStartPos})/\text{CorrectionDia}/2))*I_{EP}) + \text{OutsideEdgeStartPos}$$

wherein $I_{EP}$ is the inside edge position.

The offset position O of each slit shape is preferably determined by the slit width S and the inner edge $E_1$ position. Thus:

$$O = E_1 + S/2$$

The iris diameter I is preferably set such that the outside corners 72 of the slit shape are anchored at the outer boundary 63 of the transition zone 62. Thus, the iris diameter I will be reduced as the profiled beam is displaced radially outward (see FIG. 3A). If this cannot be achieved, the iris diameter I is set to its maximum value which will generally leave the outside corners 72 of the slit shape within the transition zone. Reducing the iris diameter as the beam moves outward provides a smoothing of the transition zone 62.

$$\text{IrisDiameter} = \sqrt{I_{EP}^2 + \text{AblationDia}^2 * O_{EP}^2 - 2*I_{EP}*O_{EP}}$$

$$\text{IrisDiameter} = \min(\text{MaximumIrisDia}, \text{IrisDiameter})$$

Thus, laser 28 is pulsed, and platform 38 and lens 51 are displaced to a successive position radially displaced from the previous position by the equations described above. The laser is again pulsed, platform 38 and lens 51 are again displaced, the laser is again pulsed, etc. This process continues until the entire correction zone 60 has been covered in incremental steps (either with one pass over the entire correction zone, two passes, each over half of the zone as shown in FIG. 3A, or a plurality of passes, each over a section of the optical zone).

Of course, it will be recognized that the rectangular ablations may be scanned or displaced across the optical correction zone in a variety of manners other than that described above. For example, the rectangular ablations may begin at one side of the optical correction zone 60 within the annular transition zone 62 (e.g., with an inner blade edge $E_3$ and an outer blade edge $E_4$, as shown in FIG. 3A). In this embodiment, the imaging lens is displaced in such as manner as to scan the cylindrical ablations across the optical correction zone to the other side of the annular transition zone.

In addition, it should be noted that the cylinder width may be maintained constant during the ablation procedure. In this embodiment, the displacement of the imaging lens 51 only provides the increased curvature on the corneal surface.

During the calculation of the positions of the offset mechanism, the actual laser pulse number is preferably mapped to a modified pulse number to produce positions of the offset mechanism that create a uniform ablation on the eye during any point in the treatment. The sort algorithm is specified by the number of layers that the complete cylinder ablation should be divided into. In one embodiment, the pulses from the two halves of the eye are arranged so that the offset motion starts at one side and moves continually across the eye to the other side. The pulses then reverse direction and move back to the original side. Each pass of the offset mechanism comprises a layer. The entire procedure will typically comprise about 5 to 15 layers, and preferably about 10 layers.

By separating the overall treatment into layers, motion of the mechanical elements within each particular layer can be optimized. Also, in the event of an interruption in the treatment before completion, the patient will be left with a partially completed ablation pattern which will be easier to align when the procedure is resumed or which is optically beneficial if the procedure cannot be resumed.

Figure 4:
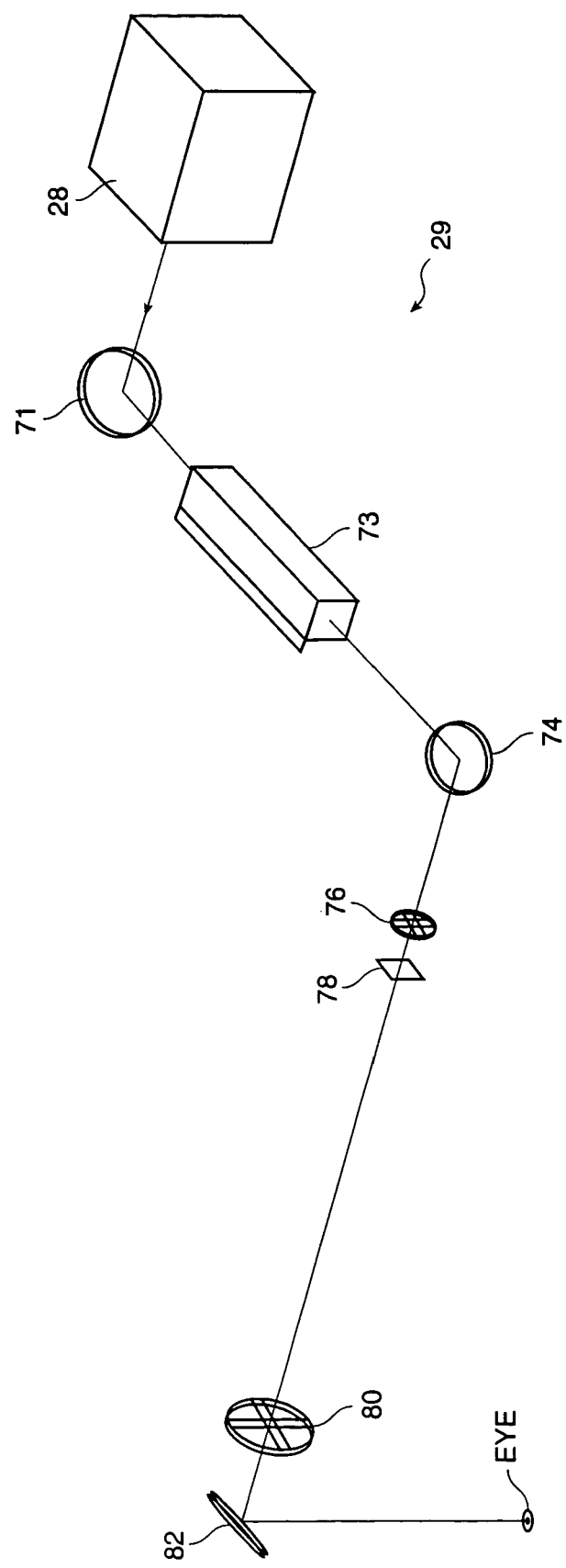
FIG. 4 is a schematic view of delivery system optics of the surgery system of FIG. 1.

FIG. 4 is a schematic view of the delivery system optics in the preferred embodiment. As seen in this figure, the beam from laser 28 is reflected by a first mirror 71 and enters a spatial and temporal integrator assembly 73, where the beam is modified in cross-section. Alternatively, the delivery optics may include a dove prism rather than a temporal beam integrator. The modified beam exiting from spatial and temporal integrator 73 is reflected by mirror 74 and passed through a lens 76 that collimates the beam, and through an iris/slit mechanism 78 which contains the variable width slit and variable diameter iris described above. The profiled beam exiting from the unit 78 enters the image offset control unit 80 which contains imaging lens 51. The offset profiled image exiting from unit 80 is reflected from a mirror 82 onto the patient's eye.

FIGS. 5 and 6 illustrate the image offset control unit 80. As shown, imaging lens 51 is contained in a fixture 81, which is mounted for pivotal motion about a first pivot post 83. Pivot post 82 is mounted in the internal recess of a fixture housing 87. A first drive motor 93 is mounted to fixture housing 87 for rotating imaging lens 51 about pivot post 83. In the representative embodiment, drive motor 93 comprises a rack and pinion drive with an arc shaped rack 94 that engages teeth (not shown) for rotating lens 51. First drive motor 93 provides rotational movement to lens 51 to vary the angle of lens 51, thereby changing the direction that lens 51 is translated. A second drive motor 89 is mounted on a flange portion 90 of housing 87 and has an output shaft 91 for driving a second drive belt 92 which is coupled to the lower portion of housing 87.

In operation, when fixture 81 is driven by motor 93, the lens 51 pivots about post 83. Similarly, motor 89 and belt 92 pivot housing 87 about flange 90 and base 92. By operating motors 89, 93 simultaneously, compound motion of fixture 81 can be effected so that both translational and rotational motion can be imparted to the lens 51. For example, if the rotational movement of lens 51 about post 82 is offset by the rotational movement of the entire fixture housing 87, purely translational movement of lens 51 occurs. Motors 89 and 97 are driven by the computer 21. By properly programming computer 21, the desired motion can be imparted to imaging lens 51 in order to scan the aperture image over the desired ablation region of the corneal surface. An alternative offset imaging mechanism is described in U.S. patent application Ser. No. 08/058,599, filed May 7, 1993 for "METHOD AND SYSTEM FOR LASER TREATMENT OF REFRACTIVE ERRORS USING OFFSET IMAGING", the complete disclosure of which has previously been incorporated herein by reference.

The invention affords great flexibility in performing various types of corrections by virtue of the fact that the system can be programmed to accommodate patients having differently sized physical eye parameters and refractive correction requirements. The slit width/variable diameter iris arrangement is particularly adaptable for use in the treatment of hyperopic astigmatism. For simultaneous treatment of hyperopia and astigmatism, the ablation geometry is solved as a function of image lens displacement and variable aperture size, as discussed above. Further, in all procedures requiring a smoothing of the transition zone at the periphery of the ablation zone, the diameter of the iris is varied over a predetermined range. For refractive aberrations, a device such as a spatially resolved refractometer or a topography machine or both may be used to map the irregular surface contour of the cornea to determine the exact surface corrections required. Thereafter, the slit width and the iris diameter can be programmed such that corneal sculpting will achieve the desired cylindrical surface geometry in the optical correction zone.

In addition to hyperopic corrections, the invention can be used for other visual error corrections, both regular and irregular, for phototherapeutic keratectomy (typically used to ablate scar tissue), and for smoothing ablations. For phototherapeutic keratectomy applications, a scar which occurs centrally over the cornea can be ablated with the excimer laser by ablating a large area with a transition zone at the edge. As in the case with astigmatism and hyperopia, it is desirable to position the transition zone as far from the optically used portion of the cornea as possible. This avoids potentially undesirable side effects of scar removal, such as hyperopic shift in which changes in the curvature of the cornea create a hyperopic condition.

For any of the above specific correction procedures, a treatment table is normally constructed containing the value of all of the discrete radial positions of the optical-mechanical elements used to scan the image over the relevant portion of the anterior corneal surface, as well as the number of laser pulses per position. A typical treatment table contains on the order of about 500 different entries.

The treatment table for a given procedure may incorporate special features designed to improve the efficiency of the procedure. For example, for some procedures (e.g., hyperopic correction) it can be beneficial to leave a small zone centered on the optical zone untreated. This can be done by constraining motion of the inner cylinder blade to guarantee occlusion in the small zone of interest. Further, compensation for variable or differential healing rates and for differential ablation depth due to tissue hydration may be factored into the treatment table.

While the invention has been described above with specific reference to ablation of the anterior corneal surface, other portions of the cornea may also be treated using the invention. For example, the epithelium may be mechanically removed by scraping, as is typically done in photorefractive keratectomy, and the exposed surface may be ablated. Further, the invention can also be used for laser keratomileusis of corneal lamella removed from the cornea. This procedure is described in U.S. Pat. No. 4,903,695 issued Feb. 27, 1990 for "METHOD AND APPARATUS FOR PERFORMING A KERATOMILEUSIS OR THE LIKE OPERATION". In applying the invention to this procedure, a flap of corneal tissue is physically removed from the cornea, the size of the removed portion typically lying in the range from about 8 to 10 mm wide and a variable thickness up to 250 microns. This flap of tissue is typically removed using a microkeratome. Next, the flap is placed in a suitable fixture—typically an element having a concave surface—with the anterior surface face down. Thereafter, the required ablation is performed on the reverse exposed surface of the flap, after which the ablated flap is repositioned on the cornea and reattached by suturing. Alternatively, after the flap is removed from the cornea, the exposed stromal tissue of the eye can be ablated according to the invention, after which the flap is re-attached over the freshly ablated stromal tissue. In other procedures, the flap is folded away from the rest of the corneal instead of being entirely removed from the cornea. In these procedures, the ablation is performed on the exposed stromal tissue, and the flap is then folded back over and re-attached to the freshly ablated stromal tissue.

While the above provides a full and complete disclosure of the preferred embodiments of the invention, various modifications, alternate constructions and equivalents may be employed as desired. For example, while the invention has been described with specific reference to the system of FIGS. 1 and 2, other systems may be employed, as desired. For example, the systems and methods described herein may be employed in conjunction with the T-PRK® scanning and tracking laser from Autonomous Technologies Corporation, the SVS Apex laser from Summit Technology Inc., the Keracor™ 117 scanning laser system from Chiron Vision, or the like. Further, lasers of other appropriate wavelengths than laser 28 may be used, if desired and effective. Also, laser beam systems which operate on the principle of thermal ablations, such as lasers having wavelengths lying in the infrared portion of the electromagnetic spectrum, may be used to implement the invention. In addition, while the radial and angular positioning of the profiled beam is accomplished with imaging lens 51 in the preferred embodiment, other optical scanning elements—such as rotating mirrors and prisms—may be employed, if desired. Therefore, the above description and illustrations should not be construed as limiting the invention, which is defined by the appended claims.

What is claimed is:

1. A system for performing selective ablation of a corneal surface of an eye to effect a desired corneal shape, the system comprising:
a laser that generates a laser beam;
delivery optics coupled to the laser that directs the laser beam onto a corneal surface of an eye;
a variable aperture element that profiles the laser beam to perform cylindrical corrections on the cornea; and
a laser beam direction system that displaces the laser beam across the cornea, wherein the laser beam direction system and the variable aperture element operate in conjunction to change the corneal surface from an initial curvature having hyperopic and astigmatic optical properties to a subsequent curvature having correctively improved optical properties, wherein the laser beam direction system comprises an imaging lens positioned between the variable aperture element and the eye, and a translational motor for translating the imaging lens along a linear direction so as to translate an image of the variable aperture element across the corneal surface.

2. A method of performing selective ablation of a corneal surface of an eye to effect a desired corneal shape, wherein the desired corneal shape includes a first section having a first depth of tissue removal and a second section having a second depth of tissue removal less than the first depth, the method comprising:
establishing an optical correction zone on a corneal surface of an eye;
directing a laser beam through an aperture to produce a profiled beam having substantially rectangular shape and a cross-sectional area smaller than the optical correction zone;
displacing the laser beam to a plurality of selected locations on the optical correction zone to effect the desired corneal shape, wherein at least a portion of a substantial amount of the selected locations covers the first section of the optical correction zone to remove corneal tissue to the first depth at the first section, and at least a portion of a lesser amount of the selected locations cover the second section to remove corneal tissue to the second depth at the second section that is less than the first depth; and
allowing the laser beam to pass through a variable diameter diaphragm and a variable width slit.

3. The method of claim 2 further comprising selectively varying the diameter of the diaphragm and the width of the slit during the displacing step.

4. A method of performing selective ablation of a corneal surface of an eye to effect a desired corneal shape, wherein the desired corneal shape includes a first section having a first depth of tissue removal and a second section having a second depth of tissue removal less than the first depth, the method comprising:
establishing an optical correction zone on a corneal surface of an eye;
directing a laser beam through an aperture to produce a profiled beam having a cross-sectional area smaller than the optical correction zone;
displacing the laser beam to a plurality of selected locations on the optical correction zone to effect the desired corneal shape, wherein at least a portion of a substantial amount of the selected locations covers the first section of the optical correction zone to remove corneal tissue to the first depth at the first section, and at least a portion of a lesser amount of the selected locations cover the second section to remove corneal tissue to the second depth at the second section that is less than the first depth;
allowing the laser beam to pass through a variable diameter diaphragm and a variable width slit; and
reducing the diameter of the diaphragm and the width of the slit as the laser beam is displaced radially outward.

5. The method of claim 4 further comprising establishing an annular transition zone outside of the optical correction zone, the annular transition zone having an outer boundary, wherein the diameter of the diaphragm is selected such that an outer edge of the profiled beam remains between the optical correction zone and the outer boundary of the transition zone.

* * * * *

UNITED STATES PATENT AND TRADEMARK OFFICE
CERTIFICATE OF CORRECTION

PATENT NO. : 7,582,081 B2 Page 1 of 1
APPLICATION NO. : 09/950563
DATED : September 1, 2009
INVENTOR(S) : Hofer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1451 days.

Signed and Sealed this

Fourteenth Day of September, 2010

David J. Kappos
*Director of the United States Patent and Trademark Office*